United States Patent [19]

Kennedy et al.

[11] Patent Number: 5,234,940
[45] Date of Patent: Aug. 10, 1993

[54] PHOTOCHEMOTHERAPEUTIC METHOD USING 5-AMINOLEVULINIC ACID AND PRECURSORS THEREOF

[75] Inventors: James C. Kennedy; Roy H. Pottier; Robert L. Reid, all of Kingston, Canada

[73] Assignee: Queen's University, Kingston, Canada

[21] Appl. No.: 865,151

[22] Filed: Apr. 8, 1992

Related U.S. Application Data

[63] Continuation-in-part of Ser. No. 783,750, Oct. 28, 1991, which is a continuation of Ser. No. 386,414, Jul. 28, 1989, Pat. No. 5,079,262.

[51] Int. Cl.⁵ ............... A61K 31/40; A61K 31/195
[52] U.S. Cl. .................... 514/410; 514/561; 514/814; 514/843; 514/899; 540/145; 424/7.1; 562/567
[58] Field of Search ............ 514/561, 410, 899, 814, 514/843; 424/7.1; 540/145; 562/567

[56] References Cited

U.S. PATENT DOCUMENTS

| | | | |
|---|---|---|---|
| 3,846,490 | 11/1974 | Aronova et al. | 562/567 |
| 3,934,369 | 1/1976 | Rebeiz | 435/240.45 |
| 3,973,129 | 8/1976 | Blumberg et al. | 250/461.2 |
| 4,772,681 | 9/1988 | Fukuda et al. | 540/145 |
| 4,977,177 | 12/1990 | Bommer et al. | 514/410 |
| 4,997,639 | 3/1991 | Aizawa et al. | 424/9 |
| 5,004,811 | 4/1991 | Bommer et al. | 540/145 |
| 5,043,101 | 8/1991 | Gordon | 252/408.1 |

FOREIGN PATENT DOCUMENTS

| | | |
|---|---|---|
| 0233701 | 8/1987 | European Pat. Off. |
| 62-63586 | 3/1987 | Japan . |
| 62-205081 | 9/1987 | Japan . |

*Primary Examiner*—Glennon H. Hollrah
*Assistant Examiner*—Gary E. Hollinden
*Attorney, Agent, or Firm*—Richard J. Hicks

[57] ABSTRACT

A method of detecting and treating malignant and non-malignant tissue abnormalities and lesions of the skin; conjunctiva; respiratory, digestive and vaginal mucosa; endometrium and urothelium; and for ablating the endometrial tissue and treating body fluids containing suspended abnormal cells, and for treating cancers of the nervous system in which 5-aminolevulinic acid or precursor thereof is administered to the patient in an amount sufficient to induce synthesis fluorescence and/or photosensitizing concentrations of of protoporphyrin IX in the abnormal cells, followed by exposure of the abnormal cells to light of photoactivating wavelengths.

8 Claims, No Drawings

PHOTOCHEMOTHERAPEUTIC METHOD USING 5-AMINOLEVULINIC ACID AND PRECURSORS THEREOF

CROSS REFERENCE TO RELATED APPLICATIONS

This application is a continuation-in-part of U.S. application Ser. No. 07/783,750 filed Oct. 28, 1991 which is a continuation of U.S. application Ser. No. 386,414 filed Jul. 28, 1989 and now U.S. Pat. No. 5,079,262 issued Jan. 7, 1992.

FIELD OF INVENTION

This invention relates to the detection and treatment of certain tissue abnormalities (both cancerous and non-malignant) by induced fluorescence and photochemotherapy respectively. The invention also relates to the detection and treatment of abnormalities in body fluids or suspensions containing abnormal cells by induced fluorescence and photochemotherapy. The invention further relates to treatment of both normal and abnormal endometrial tissue by photochemotherapy.

BACKGROUND OF INVENTION

Tissue abnormalities involving the skin usually are detected and assessed by a combination of visual inspection and palpation. In certain clinical situations the sensitivity of the visual inspection can be enhanced by the use of non-white light (either ultraviolet or a narrow band in the visible), or by the prior application of a contrast-enhancing agent such as dilute acetic acid or certain stains. Tissue abnormalities that involve surfaces that cannot be palpated (such as the bronchi or the urinary bladder) may be visualized via an appropriate scope. Some specialized scopes can detect induced fluorescence. If the abnormality in question is associated with a difference in either the extent or the pattern of tissue vascularization, such a scope may be used to determine the limits of the area involved by the abnormality, by visualizing an injected bolus of fluorescein as it passes through the vasculature of both the lesion and the adjacent normal tissue.

In addition, fluorescence-detecting scopes are being used experimentally to identify areas of tissue that show strong porphyrin fluorescence following the intravenous injection of exogenous porphyrins such as hemotophorphyrin IX (HpIX), hemotoporphyrin derivative (HpD), or "dihematoporphyrin ether". Such porphyrins tend to accumulate semi-preferentially in malignant tissues, but they also accumulate in tissues that are regenerating following injury or in the rapidly growing tissues of an embryo or fetus. Normal liver, spleen, and kidney also tend to accumulate these porphyrins. Using such compounds and fluorescence-detecting scopes, areas of malignant tissue too small to be identified by standard forms of visual inspection have been identified in the bronchi and in the urinary bladder.

Unfortunately, a clinically significant (photosensitizing) amount of porphyrin persists in the skin for at least two weeks, (occasionally for more than two months) following the intravenous injection of HpIX, HpD, or Photofrin II. This means that patients must avoid exposure to sunlight (either direct, or through window glass) for an inconveniently long period of time postinjection. Understandably, patient compliance often is poor, and accidental phototoxic "sunburn" is a common occurrence in the weeks following a diagnostic or therapeutic injection of porphyrin. Persistent photosensitivity is the major hazard associated with this technique, and is the main reason why it is not used more widely.

The standard or conventional forms of treatment for cancer comprise surgery, radiotherapy and chemotherapy. However, other forms of treatment are also known, including photochemotherapy or photodynamic therapy (PDT). PDT is currently being used, on an experimental basis, to treat several different types of cancer as well as certain non-malignant lesions such as psoriasis. The patient is given a photo-activatable drug that has some degree of specificity for the tissue being treated. A tissue volume that includes the target tissue is then exposed to photoactivating light so as to destroy the target tissue while causing only mild and reversible damage to the other tissues in the same treatment volume.

There are two main types of photochemotherapeutic agents in clinical use at present. The first type, methoxypsoralents, are given systemically. Ultraviolet light is essential to activate them. Localized exposure of psoralen-containing tissues to ultraviolet light induces a localized photochemical reaction that causes the drug to bind covalently to the DNA of living cells, thus destroying their proliferative potential. The second type, porphyrins, are also given systemically (by intravenous injection), although occasionally they are given either topically or by intralesional injection. They can be activated by visible (red) light. The localized exposure of porphyrin-containing tissues to such light ordinarily does not induce a chemical reaction between cell components and the porphyrin molecules. Instead, the porphyrins act as catalysts by trapping the energy of the photoactivating light and then passing it on to molecules of oxygen, which in turn are raised to an excited state that is capable of oxidizing adjacent molecules or structures. Cell death is not caused primarily by damage to the DNA, but by damage to essential membrane structures. Photochemotherapy is used at present for the treatment of certain types of cancer and nonmalignant lesions, including psoriasis. The goal of such treatment is sometimes cure (mainly for basal cell carcinomas), but usually the goal is palliation through local control when none of the standard forms of therapy are considered likely to offer a significant degree of benefit to the patient.

Methoxypsoralen (PUVA) therapy is used mainly for the treatment of psoriasis, but sometimes it is also used to treat very superficial cancers that involve the skin (mainly mycosis fungoides). However, there are two serious problems with such treatments. First, the procedure has been demonstrated in humans to be carcinogenic. Second, the photoactivating ultraviolet light is absorbed so strongly by most tissues that the depth at which malignant tissue can be killed is limited to a few millimeters below the illuminated surface. These problems severely limit the usefulness of the methoxypsoralens for photochemotherapy.

At present, the porphyrins most commonly used for photochemotherapy are Hematoporphyrin IX (HpIX), Hematoporphyrin derivative (HpD), and Photofrin II, a semi-purified form of HpD. When porphyrins are used as photosensitizers, cell death results from damage to cell membranes. Consequently, malignant transformation is not a serious problem. Moreover, since the visible (red) light that is used to photoactivate porphyrins penetrates tissue much more deeply than does the ultraviolet light that must be used to photoactivate methoxypsoralens, the depth at which porphyrin-treated tissue can be killed is substantially greater. Also, since certain types of porphyrins show a significant tendency to accumulate preferentially in malignant tissues, it is sometimes possible to destroy malignant tissue without causing clinically significant damage to adjacent normal tissues.

The main problem with the systemic use of HpIX, HpD and Photofrin II is that photosensitizing concentrations persist in the skin for several weeks to several months following their adminstration. Consequently, severe accidental phototoxic skin reactions may occur unless the patient avoids exposure to sunlight (either direct, or filtered through window glass) until the concentration of the photosensitizer in the skin has been reduced to a harmless level. At present, the problem of photosensitivity following the adminstration of porphyrins is handled by advising the patient to avoid any form of exposure to sunlight (or to very bright artificial lights) for a period of at least two weeks post-injection, and to initiate subsequent exposure to sunlight very cautiously. Not all patients comply with these instructions, since it often is quite inconvenient to do so. In addition, the use of a sunscreen with a high blocking factor is recommended with a warning that this will only reduce the hazard somewhat, not eliminate it completely. In a few cases, patients whose photosensitization persisted for more than a month post-treatment have been given large daily doses of beta-carotene over a period of several months in an attempt to prevent accidental phototoxic damage. Finally, attempts have been made to reduce phototoxicity by applying the photosensitizer topically to a limited area.

However, another type of problem is encountered if HpIX or HpD is applied topically in DMSO (Dimethylsulfoxide), Azone, or some other vehicle intended to enhance their diffusion through tissue. The porphyrins tend to become immobilized wherever they happened to be when the DMSO or Azone becomes diluted by normal tissue fluids to such an extent that the porphyrins can no longer diffuse through the tissue (or even remain in solution). Consequently, the topical application of porphyrins often is associated with a loss of specificity for malignant tissues, and normal tissues near the site of application may develop persistent photosensitization from the localized concentration of porphyrin.

OBJECT OF INVENTION

It is an object of the present invention to provide a method for the detection of certain types of malignant and non-malignant cell and tissue abnormalities by induced fluorescence.

It is another object of the present invention to provide a photodynamic (photosensitizing) treatment method using an agent which can be administered either systemically or topically and which is not in itself a photosensitizer but which induces the synthesis of protoporphyrin IX (PpIX) in vivo.

It is another object to provide a method of endometrial tissue ablation for the treatment of dysfunctional uterine bleeding, endometriosis, endometrial cancer, and iron deficiency anaemia caused by excessive bleeding at periods. Another object is to provide a contraceptive method, a method of sterilization or near sterilization, a method of eliminating unwanted monthly periods, and a method of early termination of pregnancy.

STATEMENT OF INVENTION

By one aspect of this invention there is provided a method for treating dysfunctional uterine bleeding, iron deficiency anaemia due to excessive menstrual bleeding, a method of sterilization or near sterilization, a method of contraception, and a method for early termination of pregnancy, in which an effective amount of precursor of protoporphyrin IX in the biosynthetic pathway for heme is administered to a patient in need of treatment so as to induce synthesis of protoporphyrin IX (PpIX) in endometrial tissue and exposing said tissue to light having a wavelength within the photoactivating action spectrum of said PpIX to thereby induce photoactivation in said tissue.

By another aspect of this invention there is provided use of a composition comprising a precursor of protoporhyrin IX in the biosynthetic pathway for heme for the manufacture of a medicament for treating malignant and non-malignant tissue abnormalities and lesions of the skin, mucosa, exocrine glands and ducts, gonads, thymus, spleen, lymph, blood and the nervous system.

In preferred aspects of this invention the preferred precursor of protoporphyrin IX is 5-amino-4-oxo-pentanoic acid, otherwise known as 5-aminolevulinic acid, and a preferred wavelength of the photoactivating light is in the range 350–640 nm, more preferably a red light of 625 nm.

DETAILED DESCRIPTION OF PREFERRED EMBODIMENT

Protoporphyrin IX (PpIX), a naturally occurring photosensitizer, is the immediate precursor of heme in the heme biosynthetic pathway. All nucleated cells have at least a minimal capacity to synthesize PpIX, since heme is necessary for the synthesis of various essential heme-containing enzymes. Certain types of cells and tissues can synthesize relatively large quantities of PpIX. Under normal conditions, the synthesis of PpIX in such tissues is under such tight feed-back control that the cells produce it at a rate just sufficient to match their need for heme. However, the usual rate-limiting step in the process, the synthesis of 5-aminolevulinic acid (ALA), can be bypassed by the provision of exogenous ALA, porphobilinogen, or other precursor of PpIX. Certain tissues and organs will then accumulate such a large excess of PpIX that they become both fluorescent and photosensitive. At least in the case of the skin, the PpIX appears to be synthesized in situ. The ALA, which is commercially available from Sigma Chemical Company and other sources and which is water soluble, can be administered orally, topically or by injection. The oral and parenteral routes lead to the induction of clinically useful concentrations of PpIX in certain benign and malignant tissues throughout the body. Only certain types of tissue synthesize and accumulate clinically useful amounts of PpIX when provided with an excess of ALA. At the present time, treatment of basal cell, baso-squamous and squamous cell carcinomas and other lesions of the skin, mucosa (respiratory, digestive, and vaginal), endometrium and urothelium is contemplated. Sites could include lesions or cellular abnormalities involving (i) skin and conjunctiva; (ii) the lining of the mouth, pharynx, esophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tissues or suspensions of body fluids containing abnormal cells, including blood, that can be made accessible to photoactivating light either in vitro, at time of surgery, or via an optical fibre inserted through a needle; (x) all exocrine glands and associated ducts, including: mammary glands, sebaceous glands, ceruminous glands, sweat glands, and lacrimal glands; mucus-secreting glands of the digestive, urogenital, and respiratory systems; salivary glands; liver, bile ducts, and gall bladder; pancreas (exocrine component); gastric and intestinal glands; prostate; Cowper's, Bartholin's, and similar glands. It is also contemplated that cell abnormalities in the gonads (testes and ovaries), thymus, spleen, lymph nodes, bone marrow, lymph and blood may also be treated according to the invention. Tumours of the nervous system or connective tissues (sarcomas) may also be treated according to this invention.

Treatment of non-malignant lesions such as genital warts and psoriasis and other indications of the endometrium, such as contraception, vaginal bleeding, abortion and sterilization is also contemplated. In effect, an alternative to hysterectomy is within the scope of this invention.

As used herein the term "skin" includes:

(A) the covering of the external surface of most of the body, commonly termed the skin.

(B) the covering of the external genitalia:
labia majora, labia minora, clitoris, and associated structures
glans penis, prepuce, and associated structures (C) the covering of the zone of transition between skin and the mucosa of the digestive system:
anal verge
vermillion border of the lips (D) the lining of the external auditory meatus, and the covering of the external surface of the tympanic membrane (E) all exocrine glands and associated ducts that are located at least partially within an epidermal surface described above, or within the underlying dermis.

The term "mucosa" includes:

(A) the lining of the whole of the respiratory tract:
nasal passages and nasal sinuses
nasal pharynx and associated structures
larynx, vocal cords, and associated structures
trachea, bronchi, and bronchioles (B) the lining of the whole of the digestive tract:
oral cavity and tongue
oral pharynx and laryngeal pharynx
esophagus
stomach
small intestine
large intestine, caecum, and appendix
sigmoid colon and rectum
anal canal (C) the lining of the whole of the urogenital tract:
urethra, bladder, and ureters
renal pelvis and renal calyces
vagina, uterine cervix, uterus, and Fallopian tubes
vas deferens, seminal vesicles, ejaculatory duct, ampulla of vas, epididymis, and associated structures (D) the conjunctiva and the lining of the tear ducts.

(E) all exocrine glands and associated ducts that are located at least partially within one of the mucosal surfaces described above, or within the underlying submucosa.

The wavelength of the photoactivating light is of some importance, as it has been shown that between 1 and 10 percent of incident red light (600–700 nm) can pass through a slab of human tissue 1 cm thick, whereas only 0.001 percent or less of blue light (about 400 nm) can pass through the same thickness of human tissue. The photosensitizer will, therefore, be more successful if it absorbs red light. PpIX does strongly absorb red light. The present approach has several advantages over the prior art. First, PpIX has a much shorter half-life (of the order of 2 hours) in normal tissues (human and mouse, at least) than does HpIX, HpD or Photofrin ® II (half-life approximately 1 week). This greatly reduces the danger of accidental phototoxic skin reactions in the days following treatment. Second, the ALA can be applied topically to certain types of lesions. This improves the specificity of the treatment, reduces the danger of accidental phototoxic reactions to a very low level, and greatly reduces the amount of both ALA and PPIX to which the entire body would be exposed if an equally effective dose of ALA were to be given systemically. Both ALA and PpIX are normal products of metabolism, and are handled quite readily by the biochemical machinery of the body. However, since very large doses of ALA (like large doses of HpIX or HpD) are associated with a transient decrease in motor nerve conduction velocity, it is desirable to reduce the dose of ALA to the minimum that is still effective. Topical application requires much less ALA than systemic administration. Third, PpIX is rapidly inactivated by the photoactivating light. Following exposure of tissues containing PpIX to a therapeutic dose of photoactivating light, there is a substantial decrease in photosensitization of the tissues within the treatment volume. Consequently, if PpIX is induced by the topical application of ALA to specific lesions, the patient can be exposed to sunlight immediately post-treatment without danger of serious phototoxicity. Also, the dosimetry of the photoactivating light is greatly simplified. Fourth, ALA is an effective inducer of PpIX when given by mouth, by topical application, or by injection. In contrast, HpIX, HpD and Photofrin II are effective in most situations only when given by injection. This versatility of ALA enhances its acceptability for routine use by the medical profession, since the oral and topical routes of administration are much more convenient than the parenteral. Fifth, the normal and abnormal tissues that can be photosensitized by the administration of ALA are somewhat different from those that can be photosensitized by the administration of HpIX, HpD or Photofrin II. Consequently, ALA may be useful in clinical situations in which the other photosensitizers are not.

Thus the present technique is not merely another way to do what can be done already but is, in fact, a significant advance in therapeutic capability.

EXAMPLE 1

In rats ALA was injected at doses ranging from 1 to 50 mg directly into one horn of the didelphic rat uterus to minimize systemic photosensitization. The contralateral horn was injected with saline alone so that a paired comparison could be made. At a site 0.5 cm above the uterine bifurcation, ALA (Sigma Chemical Company, St. Louis, Mo.) was injected into the right uterine horn using a 1 ml tuberculin syringe with a 26 gauge needle (Bectin Dickinson and Company, Rutherford, N.J.). The rats were allowed to recover and the uterus was removed 3 hours after ALA injection and tissues were processed for either fluorescent microscopy or spectrophotofluorometry.

In other studies, 51 rats were divided into three different groups of 17 rats. The animals were anaesthetized with ether and a 3 cm incision was made through the anterior abdominal wall 1 cm rostral to the symphysis pubis. ALA dosages of 4, 8, or 16 mg in 0.1 ml saline were administrated into one horn and an equivalent volume of saline was injected into the contralateral horn. The abdomen was closed and the rats were allowed to recover from the anaesthesia. Three hours later, 9 rats from the 4 or 16 mg ALA treated group, and 8 rats from the 8 mg ALA treated group were anaesthetized with ether. The sutures were removed and the incision was opened and extended 3 cm along the midline. The intestines were pushed away with a saline soaked gauze so that both uterine horns could be exposed for 30 minutes to red light from a 500 watt CBA halogen lamp (Kodak, Carousel 860 projector, Rochester, N.Y.) equipped with a red filter (Hoya K-60, Tokyo, Japan) positioned 15 cm from the tissue (approximately 150 joules per $cm^2$). The uterine horns were kept moistened with saline. The abdomen was then closed and the rats were allowed to recover. 10 days later all rats (including those not exposed to light) were bred to a fertile male. Mating was confirmed by the presence of either a sperm plug or the presence of sperm in vaginal smears. Another control group consisted of 4 rats in whom a unilateral pregnancy was achieved by ligating one horn at its distal end prior to breeding. 10-15 days after breeding, rats were killed by decapitation. The abdomen was opened to confirm pregnancy and to determine the number and location of fetuses. Both uterine horns were harvested and preserved in 10% formalin. The nonpregnant uterine horns were dissected and histologically processed. The results are noted in Table 1 below.

TABLE 1

| Fertility Assessment 10-20 Days after ALA | | | | | | |
|---|---|---|---|---|---|---|
| ALA DOSE (MG) | 4 | 4 | 8 | 8 | 16 | 16 |
| LIGHT EXPOSURE (30 minutes) | NO | YES | NO | YES | NO | YES |
| N/GROUP* | 8 | 9 | 9 | 8 | 8 | 9 |
| PREG./SALINE- | 1 | 9/9 | 9/9 | 8/8 | 8/8 | 9/9 |
| PREG./ALA+ | 8/8 | 1/9 | 6/9 | 0.8 | 5/8 | 0.9 |

Administration of 4 mg of ALA without light had no effect on fertility. Pregnancy occurred in 8 of 8 uterine horns treated with ALA and 7 of 8 uterine horns treated with saline. In contrast, rats exposed to light following the treatment with 4 mg ALA exhibited compromised fertility. Only 1 pregnancy occurred in 9 uterine horns treated with ALA whereas fetuses were present in 9 of 9 uterine horns treated with saline. Somewhat different results occurred in rats treated with either 8 or 16 mg of ALA. In absence of light, fetuses occurred in all uterine horns treated with saline (n=17) and 6 of 9 uterine horns treated with 8 mg ALA and 5 of 8 uterine horns treated with 16 mg ALA. When the uterus was exposed to light following treatment of 8 mg ALA or 16 mg ALA or saline, all pregnancies were restricted to the saline-treated side. No pregnancies occurred in the ALA treated side.

EXAMPLE 2

Long Term Photodynamic Endometrial Ablation

In another experiment, rats were divided into 2 groups (6 and 7 rats/group) and injected with 4 or 8 mg ALA. Example 6 was repeated with the exception that all rats were exposed to light and the time from ALA administration to breeding was extended from 10-20 days to 60-70 days. All other procedures were identical to Example 1.

Breeding 60-70 days after photodynamic treatment with 4 mg ALA resulted in no implantations in the uterine horns treated with ALA (n=6) whereas fetuses were found in all control uterine horns treated with saline (n=6). These results confirmed the long term endometrial ablative effect of PDT. In the group of rats (n=7) treated with 8 mg ALA 2 of 7 became pregnant in ALA treated uterine horns compared with 7 of 7 pregnancies in the saline treated horns.

Histology

In order to show normal uterine histology of a nonpregnant uterine horn contralateral to a pregnant uterine horn one uterine horn was ligated at its distal end prior to breeding. At gestation of 10-15 days nonpregnant uterine horns were harvested and histologically processed. The uterine mucosa was lined with columnar epithelium and there was hypertrophic unfolding of endometrial tissue with tortuous glands. In contrast, prior photodynamic treatment with ALA consistently resulted in an atrophic endometrium despite the hormonal stimulus of the contralateral pregnancy.

EXAMPLE 3

In Vitro Assessment of Human Endometrial Fluorescence after Treatment with ALA

Slices (one-half mm) of human uterine tissue were prepared so as to include both myometrium and endometrium. Tissues were incubated at 37° C. in a $CO_2$ incubator with 0, 1, 10 or 100 mM ALA for 2 hours. Slides were prepared and covered and the emission fluorescence spectrum was determined using a spectrophotofluorimeter (Princeton Instruments Inc., Princeton, N.J.). The fibre optic head was positioned 1 cm from the tissue surface. No fluorescence was observed in the control (0 mM) sample or in any of the myometrial samples. Sharp fluorescent peaks at a wavelength of 640 mM were observed in the 1, 10 and 100 mM ALA treated samples of endometrial tissue. 10 and 100 mM ALA samples yielded peak fluorescence (calculated by subtracting background fluorescence from the zenith) at the two hour incubation level. Fluorescence after a 5 hour incubation was slightly lower.

EXAMPLE 4

The procedures of Example 9 were repeated with 1, 2, 3, 4 and 5 hour incubation periods using a level of 1 mM of ALA. No significant fluorescence was observed in the myometrial samples or in the endometrial samples incubated for 2 hours. Peak fluorescence was observed in the endometrial samples incubated for 4 hours.

EXAMPLE 5

Endometrial Fluorescence in Vivo following Topical Application of ALA in the Non-human Primate 50 mg of ALA was injected into the uterine lumen of an adult, healthy, female rhesus monkey following exposure of the uterus at laparotomy. A hysterectomy was performed 3 hours later and cross sectional slices incorporating endometrial and myometrial tissue were taken from the uterine specimen. These slices were subjected to fluoroscopic examination as in Example 7, 8 and 9 above. Fluorescence was observed throughout the endometrium of all slices. No fluorescence was observed in the myometrium.

The above examples clearly illustrate that endometrial ablation in a range of animal species, including humans, by photodynamic therapy using ALA can be achieved with little or no damage to the underlying myometrial tissues. This offers a possible alternative to hysterectomy and may be used as a method of contraception and/or a method for aborting an early pregnancy.

We claim:

1. A method for creating malignant and non-malignant cellular abnormalities of the endometrium and gonads in a patient comprising administering to said patient an effective amount of a precursor of protoporphyrin IX in the biosynthetic pathway for heme so as to induce synthesis of protoporphyrin IX in said abnormalities, and exposing said abnormalities to light within the photoactivating action spectrum of said protoporphyrin IX.

2. A method as claimed in claim 1 wherein said precursor of protoporphyrin IX is 5-aminolevulinic acid or a precursor thereof.

3. A method for treating dysfunctional uterine bleeding, endometriosis, iron deficiency anemia caused by excessive menstrual bleeding in a patient comprising administering to said patient a precursor of protoporphyrin IX in the biosynthetic pathway for heme, so as to induce synthesis of protoporphyrin IX in endometrial tissues in said patient, and exposing said tissues to light within the photoactivating spectrum of said protoporphyrin IX.

4. A method for sterilizing a patient comprising administering to said patient a precursor of protoporphyrin IX in the biosynthetic pathway for heme, so as to induce synthesis of protoporphyrin IX in endometrial tissues in said patient, and exposing said tissues to light within the photoactivating spectrum of said protoporphyrin IX.

5. A contraceptive method for female patients comprising administering to said patient a precursor of protoporphyrin IX in the biosynthetic pathway for heme, so as to induce synthesis of protoporphyrin IX in endometrial tissues in said patient, and exposing said tissues to light within the photoactivating spectrum of said protoporphyrin IX.

6. A method as claimed in claim 3 wherein said precursor is 5-aminolevulinic acid or precursor thereof.

7. A method as claimed in claim 4 wherein said precursor is 5-aminolevulinic acid or precursor thereof.

8. A method as claimed in claim 5 wherein said precursor is 5-aminolevulinic acid or precursor thereof.

* * * * *

UNITED STATES PATENT AND TRADEMARK OFFICE
CERTIFICATE OF CORRECTION

PATENT NO. : 5,234,940
DATED : 10 August 1993
INVENTOR(S) : J.C. Kennedy et al

It is certified that error appears in the above-indentified patent and that said Letters Patent is hereby corrected as shown below:

Column 8, line 63 reference is made to Example 9. This should read "Example 3".

Column 9, lines 12-13 reference is made to "Examples 7,8 and 9 above". This should read "Examples 3 and 4 above".

Column 9, line 25 in claim 1 it is referred to as "A method for creating malignant and non-malignant cellular abnormalities". This should read "A method for treating malignant and non-malignant cellular abnormalities".

Signed and Sealed this

Twelfth Day of July, 1994

*Attest:*

BRUCE LEHMAN

*Attesting Officer*     *Commissioner of Patents and Trademarks*